United States Patent
Chang

(10) Patent No.: US 6,761,324 B2
(45) Date of Patent: Jul. 13, 2004

(54) VACUUM GUN FOR A SUCTION DEVICE

(76) Inventor: Ti-Li Chang, 9F-7, No. 1, Lane 641, Shen-Lin S. Rd., Ta Ya Hsiang, Taichung Hsien (TW)

(*) Notice: Subject to any disclaimer, the term of this patent is extended or adjusted under 35 U.S.C. 154(b) by 217 days.

(21) Appl. No.: 10/170,697

(22) Filed: Jun. 14, 2002

(65) Prior Publication Data

US 2003/0236486 A1 Dec. 25, 2003

(51) Int. Cl.⁷ .............................. B05B 7/02; B05B 9/01; B05B 15/08
(52) U.S. Cl. ..................... 239/526; 239/525; 239/581.1; 239/587.1
(58) Field of Search ................................. 239/525, 526, 239/569, 570, 571, 583, 538, 581.1, 587.1, 587.2, DIG. 13, 165, 166, 578; 15/414, 353, 327.2, 334, 339

(56) References Cited

U.S. PATENT DOCUMENTS

| | | | |
|---|---|---|---|
| 3,698,641 A | * | 10/1972 | Lonardo ...................... 239/434 |
| 4,568,011 A | * | 2/1986 | DeArmitt et al. .......... 228/20.5 |
| 5,551,603 A | * | 9/1996 | Woodruff ..................... 222/325 |
| 5,685,039 A | * | 11/1997 | Hamada et al. .............. 15/88.2 |

* cited by examiner

Primary Examiner—Davis Hwu
(74) Attorney, Agent, or Firm—Rosenberg, Klein & Lee

(57) ABSTRACT

A vacuum gun for a suction device consists of a piston housing (10), a suction control knob (20) and a rear housing (40) with a handle (42) and a trigger (43). The piston housing has (10) multiple vacuum breaker holes (13) defined to communicate with the inside of the piston housing (10) in a row. The suction control knob (20) is rotatably mounted on the piston housing (10) to selectively block the vacuum breaker holes (13) to control the amount of suction generated during each stroke of the piston. Additionally, the handle and the trigger are foldable toward the piston housing (10) to make the vacuum gun easy to store.

7 Claims, 9 Drawing Sheets

VACUUM GUN FOR A SUCTION DEVICE

BACKGROUND OF THE INVENTION

1. Field of the Invention

The present invention relates to a vacuum gun for a suction device, and more particularly to a vacuum gun used with a hand held portable suction device that is handy and space-saving.

2. Description of Related Art

A suction device provides quick and effective pharyngeal and tracheal suction during multiple types of emergencies. With reference to FIGS. 6 to 9, a conventional suction device is a light and portable, can be operated with one hand and allows the other hand to be free for other important uses. The conventional suction device comprises an adapter (80) and a vacuum gun (60).

The vacuum gun (60) comprises a front piston housing (61), a rear housing (62), a handle (70) and a trigger (71).

A piston (63) with a front face (not numbered) and a rear face (not numbered) is slidably mounted inside the front piston housing (61) to generate a suction force on the adapter (80). A dividing wall (not numbered) is formed between the front piston housing (61) and the rear housing (62). A piston shaft (64) is formed on and extends from the piston (63). A free end of the piston shaft (64) penetrates the dividing wall and extends into the rear housing (62). A drive shaft (not numbered) is formed on the free end of the piston shaft (64), and a transverse drive rod (not numbered) protrudes from the drive shaft. Additionally, a spring (not numbered) is mounted around the piston shaft (64) between the dividing wall and the rear face of the piston to make the piston (63) move forward automatically.

The rear housing (62) has a rear wall (not numbered), a top and a bottom. A drive lever (65) is pivotally mounted inside the rear housing (62) at a middle portion of the drive lever (65) and has two moveable ends (not numbered). A longitudinal slot (not numbered) is formed on one end, and a transverse link pin (not numbered) is installed near the other end. The transverse drive rod on the drive shaft freely slides in the longitudinal slot so the pivotal movement of the drive lever (65) will cause the drive shaft and the piston shaft (64) to move longitudinally inside the vacuum gun (60). The transverse link pin in the other end of the drive lever (65) freely moves in a drive slot formed in an inner end of the trigger (71). Therefore, squeezing the trigger (71) pivots the drive lever (65) that pulls the drive shaft, the piston shaft (64) and the piston (63) toward the rear wall. The piston (63) moves a distance in the front piston housing (61) called piston travel. The physical configuration and limitations on the movement of the piston (63) determine maximum travel. A travel adjustment knob (66) with a 100% and 50% positions is rotatably mounted on an outer surface of the rear wall of the rear housing (62), and an adjusting post (67) is connected to the travel adjustment knob (66). The adjusting post (67) extends toward the piston shaft (64) and is composed of a first stop plate (68) and second stop plate (69) that are longitudinally perpendicular to each other. The first stop plate (68) and second stop plate (69) have different longitudinal lengths to limit the piston travel to 100% and 50% of the maximum travel, respectively. The handle (70) is formed on and extends from the bottom of the rear housing (62) for a user to grip the vacuum gun (60).

To operate the suction device, the trigger (71) of the vacuum gun (80) is squeezed to pivot the drive lever (65). Then the longitudinal slot in the drive lever (65) is drawn backward to make the piston (63) move backward with the drive shaft until the drive shaft reaches the adjusting post (67). Moreover, the drive shaft can be selectively stopped by the first stop plate (68) or the second stop plate (69) at different positions to control the amount of air sucked from the adapter (80). The travel adjustment knob (66) rotates to decide which stop plate (68,69) will limit the movement of the drive and piston shaft (64).

However, the conventional vacuum gun (60) has the following drawbacks.

1. Because the piston shaft (64) is stopped by the first and second stop plates (68, 69), the trigger (71) cannot be squeezed completely when the travel adjustment knob (66) is in the 50% travel position. When the travel adjustment knob (66) is in the 50% travel position, the adjusting post (67) stops the piston shaft (64) at the first top plate (68). This can lead to improper operation of the vacuum gun (60) and cause doubt concerning the operability of the vacuum gun (60).

2. The handle (70) and the trigger (71) protrude out of the rear housing (62) and take a lot of space. Therefore, the vacuum gun (60) is inconvenient to store.

The present invention has arisen to mitigate and/or obviate the disadvantage of the conventional vacuum gun for a suction device.

SUMMARY OF THE INVENTION

The main objective of the invention is to provide a vacuum gun for a suction device that is easy to use.

Other advantages and novel features of the invention will become more apparent from the following detailed description when taken in conjunction with the accompanying drawings.

DETAILED DESCRIPTION OF THE PREFERRED EMBODIMENT

Figure 1:
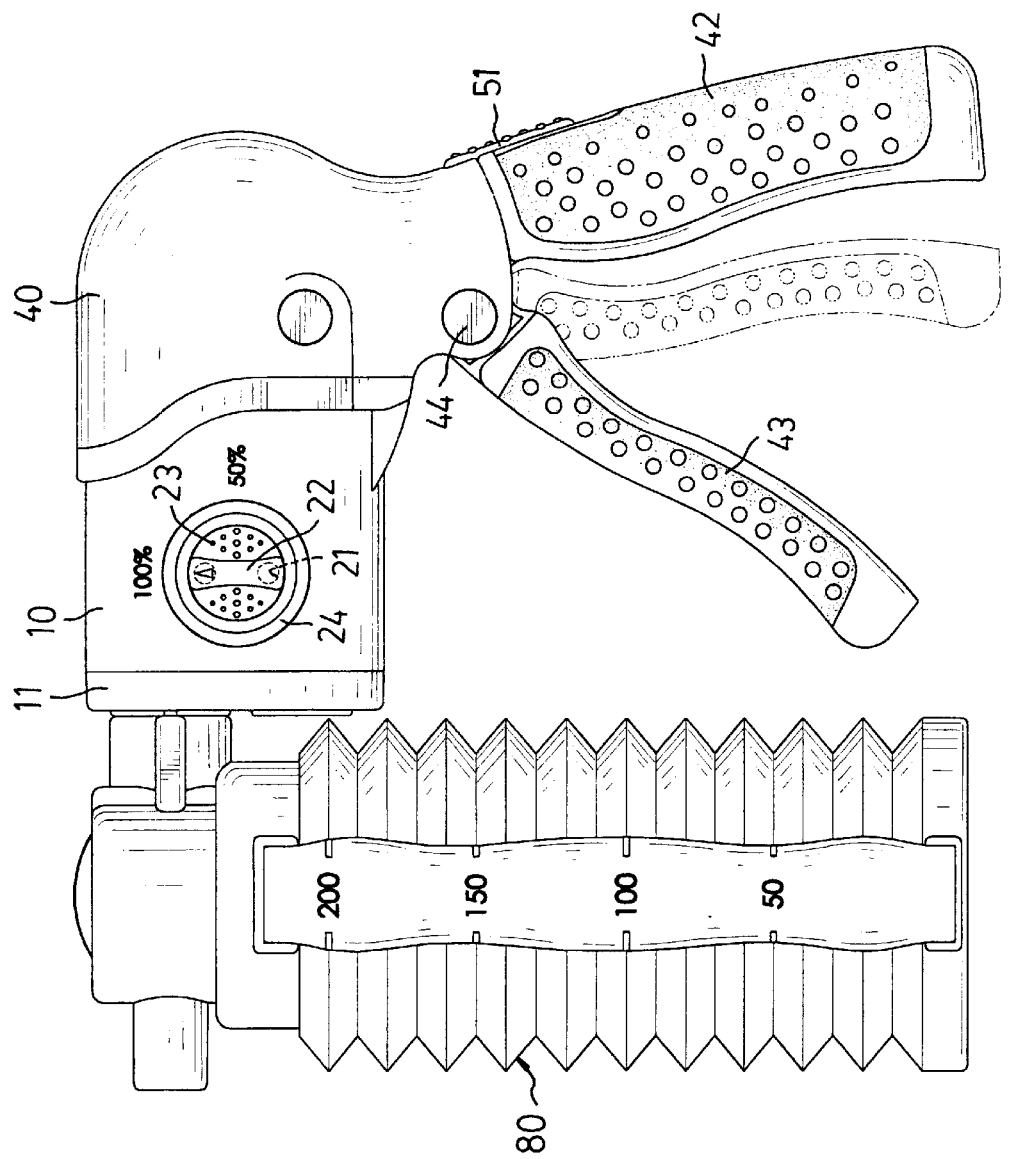
FIG. 1 is a side plan view of a vacuum gun for a suction device in accordance with the present invention.
Figure 2:
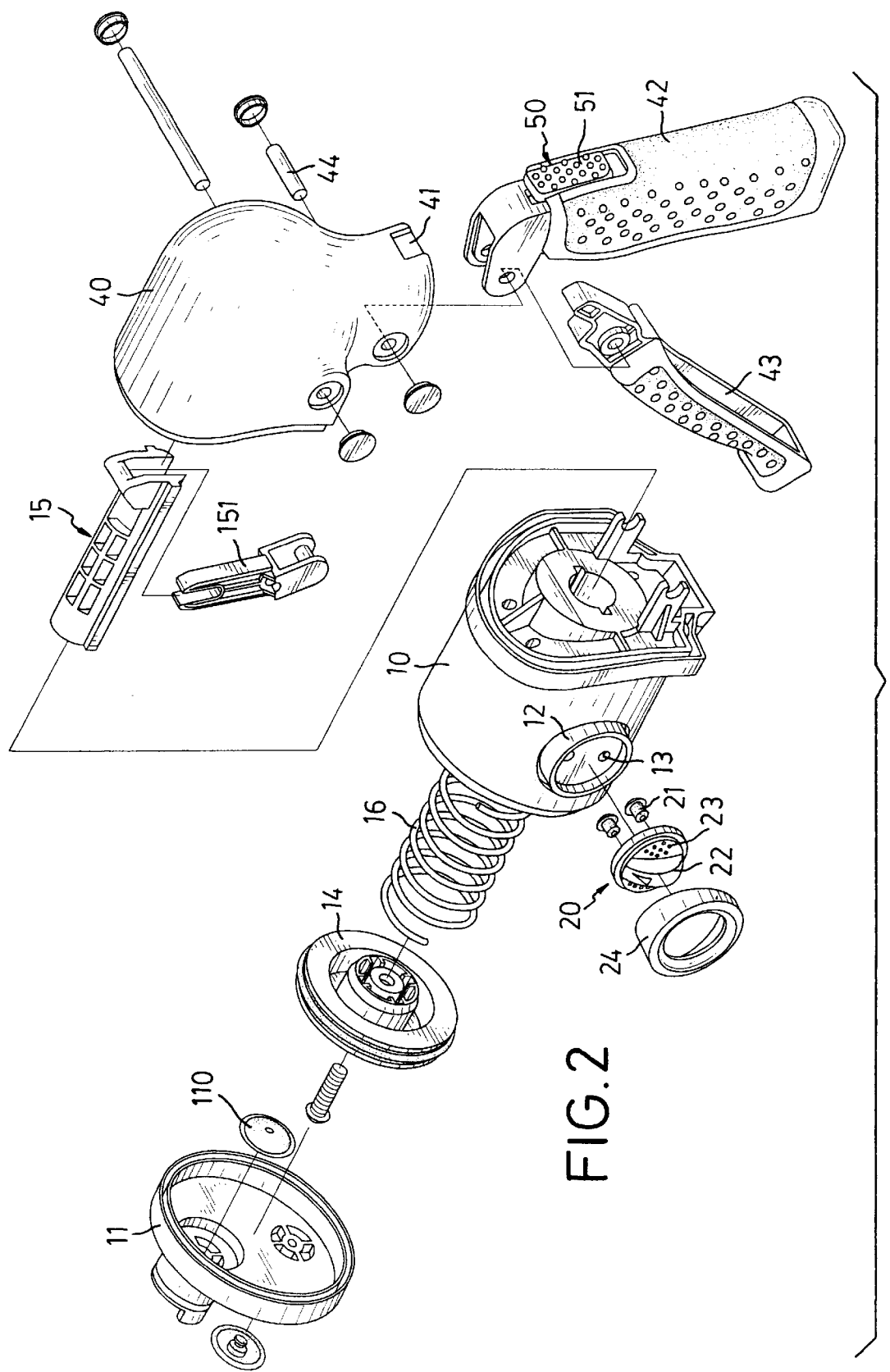
FIG. 2 is an exploded perspective view of the vacuum gun for a suction device in FIG. 1.
Figure 3:
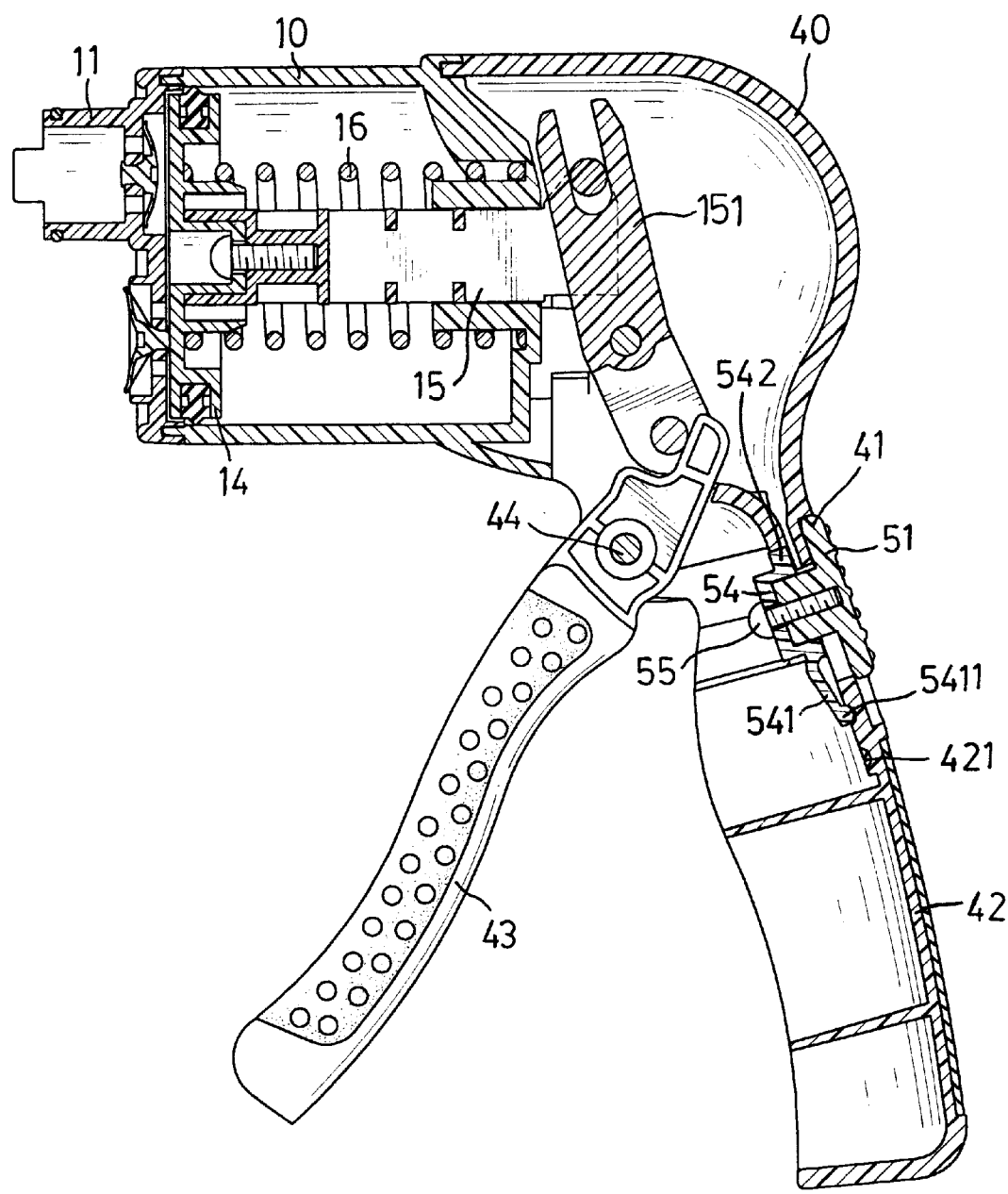
FIG. 3 is a cross-sectional side plan view of the vacuum gun in FIG. 1.

With reference to FIGS. 1 to 3, a vacuum gun for a suction device that engages an adapter (80) comprises a piston housing (10), a suction control knob (20), a rear housing (40) with a handle (42) and a trigger (43) and a handle lock (50).

The piston housing (10) has a front opening, a rear dividing wall (not numbered) and a longitudinal sidewall.

The rear dividing wall has a front and rear face, and the longitudinal sidewall has an inside surface and an outside surface. A cap (11) covers the front opening in the piston housing (10). A suction opening (not numbered) and an exhaust opening (not numbered) are formed in the cap (11). A connector (not numbered) extends out from the suction opening to attach to the adapter (80). A check valve (110) is mounted over the suction opening to only allow air to be drawn into the piston housing through the suction opening. Another check valve (not numbered) is mounted over the exhaust opening to only allow air to be discharged through the exhaust opening.

A knob holder (12) is formed on the outside surface of the piston housing (10) sidewall. The knob holder (12) comprises a flat, central, recessed face (not numbered), an annular ridge (not numbered) and multiple vacuum breaker holes (13) defined in the flat face in a vertical row to communicate with the inside of the piston housing (10). The annular ridge is formed around the flat face.

A piston (14) is movably mounted inside the piston housing (10). One end of a drive shaft (15) having two ends is rigidly attached to the piston (14), and the drive shaft (15) penetrates the dividing wall so the other end is inside the rear housing (40). A resilient element such as a spring (16) is mounted around the drive shaft (15) inside the piston housing (10) between the piston (14) and dividing wall to cause the piston (14) to move forward automatically.

The suction control knob (20) is rotatably mounted in the knob holder (12) to control the suction generated in the piston housing (10) to 50% or 100% of the distance the piston (14) moves, known as piston travel, and has a top surface (not numbered). A check valve (21) is secured inside each vacuum breaker hole (13) in the knob holder (12). Multiple ventilating holes (23) are defined in the suction control knob (20) to selectively communicate with the vacuum breaker holes (13) when the suction control knob (20) is in the 50% position. A switch bar (22) is formed on the top surface of the suction control knob (20) for user to turn the suction control knob (20) and blocks the vacuum breaker holes (13) when the suction control knob (20) is in the 100% position. A frame (24) is securely mounted on the annular ridge of the piston housing (10) and holds the suction control knob (20) against the flat face of knob holder (12) on the piston housing (10).

The rear housing (40) is attached to the piston housing (10) and has an inner and outer surface. The handle (42) and the trigger (43) are pivotally connected to the rear housing (40) by a pin (44). The handle (42) has a rear surface and two side surfaces. A drive lever (151) is rotatably mounted in the rear housing (40) and has two ends (not numbered). One end has a longitudinal slot (not numbered) and is pivotally connected to the drive shaft (15). The other end has a transverse pin (not numbered) between two longitudinal extensions, which abuts the trigger (43). Thus, the drive lever (151) can be rotated to pull the drive shaft (15) and the piston (14) by squeezing the trigger (43).

The handle lock (50) rigidly holds the handle (42) in an extended position when the vacuum gun is to be used. The handle lock (50) comprises a slide (51) and a resilient stop (54). The slide (51) is movably mounted on the rear surface of the handle (42) near a joint between the rear housing (40) and the handle (42) and has an inner protrusion (not numbered) that extends through an elongated hole (not numbered) defined through the rear surface of the handle (42). The resilient stop (54) is attached to the slide (51) by a screw (55). A notch (41) is defined in the rear housing (40) near the joint corresponding to the slide (51). The slide (51) is pushed into the notch (41) to keep the handle (42) from pivoting toward the piston housing (10). The resilient stop (54) comprises a handle stop (542) and a slide lock (541). The handle stop (542) is integrally formed on the resilient plate (54) and extends toward the rear housing (40) to abut the inner surface of the rear housing (40) when the handle (42) is extended. Therefore, the handle stop (542) presses against the rear housing (40) to stop the handle (42) from rotating further toward the rear housing (40). The slide lock (541) is integrally formed on the resilient stop (54) opposite to the handle stop (542), and a stub (5411) is formed on a distal end of the slide lock (541). At least one detent (421) is defined on the inner surface of the handle (42) to correspond to the stub (5411) on the slide lock (541).

Figure 4:
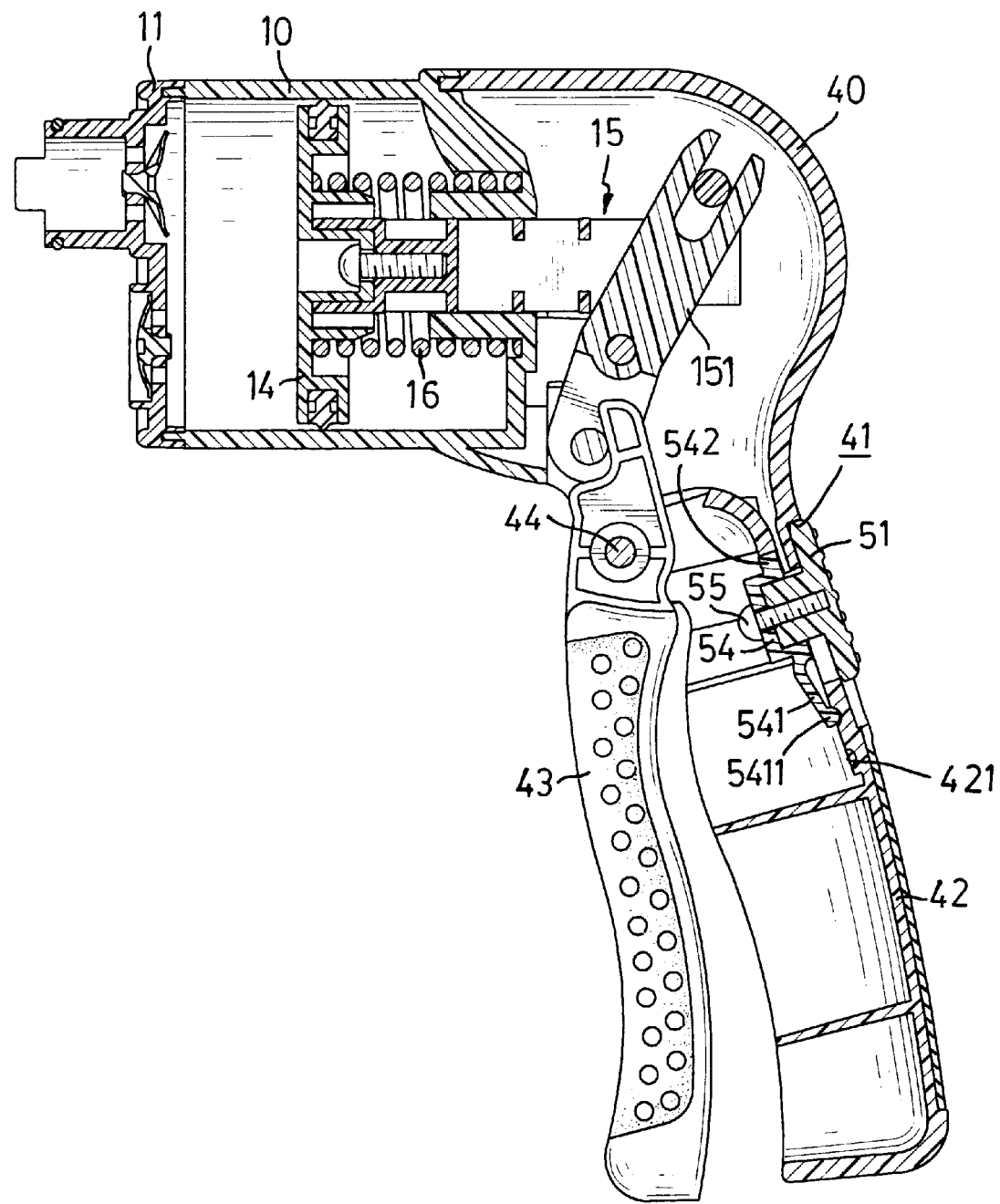
FIG. 4 is an operational cross-sectional side plan view of the vacuum gun in FIG. 1.

With reference to FIGS. 2, 3 and 4, to operate the vacuum gun, the trigger (43) is squeezed toward the handle (42) to rotate the drive lever (151). The drive shaft (15) is simultaneously pulled backward to move the piston (14) backward in the piston housing (10). When the suction control knob (20) is in the 100% position, the switch bar (22) blocks the vacuum breaker holes (13) in the knob holder (12). Therefore, only air from the adapter (80) is drawn into the piston housing (10) when the piston (14) moves inside the piston housing (10). When the suction control knob (20) is in the 50% position, the ventilating holes (23) are aligned with the vacuum breaker holes (13) in the knob holder (12). Therefore, when the piston (14) passes beyond the vacuum breaker holes (13) as it travel backward in the piston housing (10), air is drawn through the vacuum breaker holes (13) from the outside environment and not from the adapter (80) at the moment. Thereby, the quantity of air sucked through the adapter (80) is reduced and the trigger (43) can still be squeezed completely to make the vacuum gun handy in use.

Figure 5:
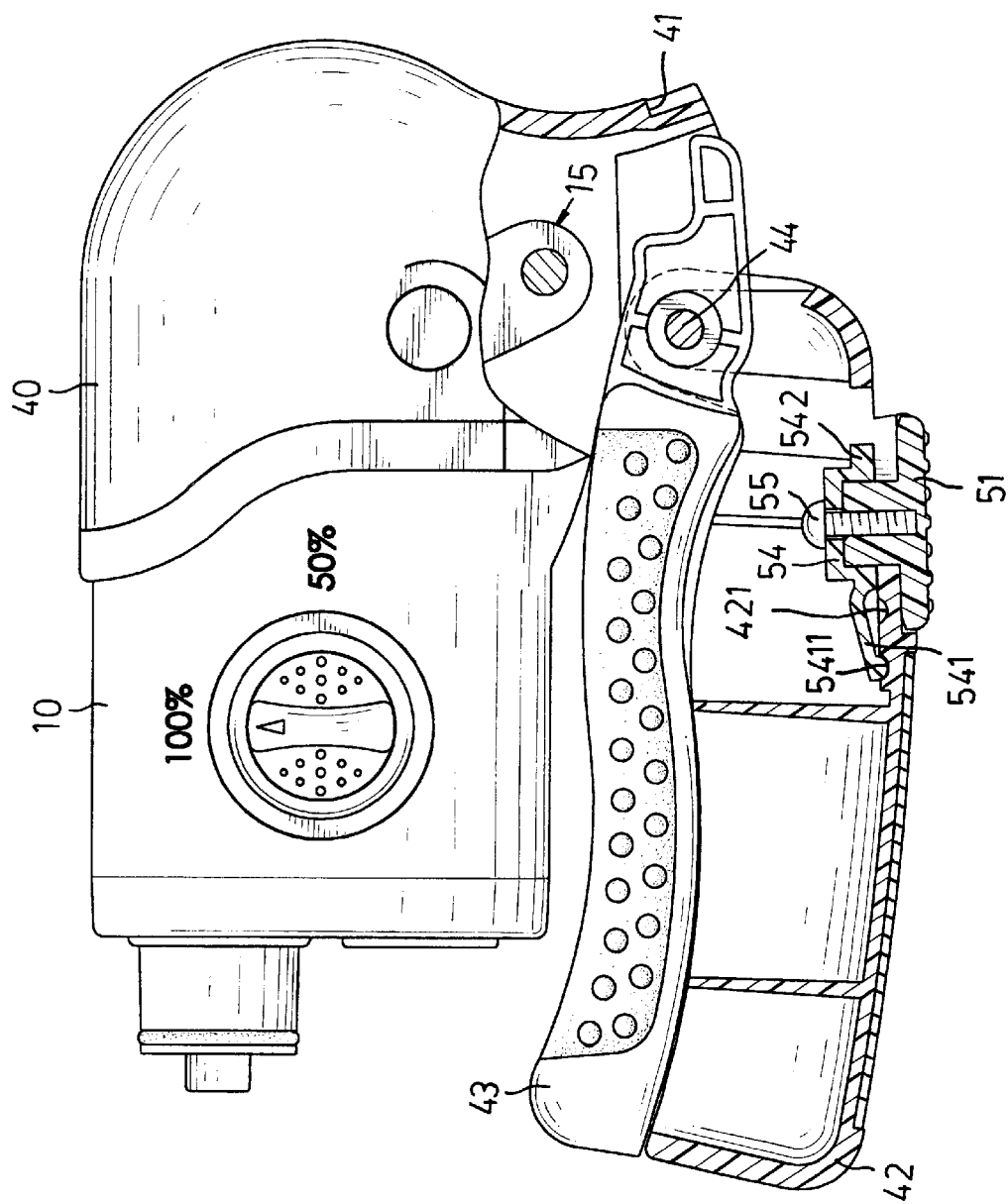
FIG. 5 is an operational side plane view of the vacuum gun in FIG. 1 with the handle and trigger folded.
Figure 6:
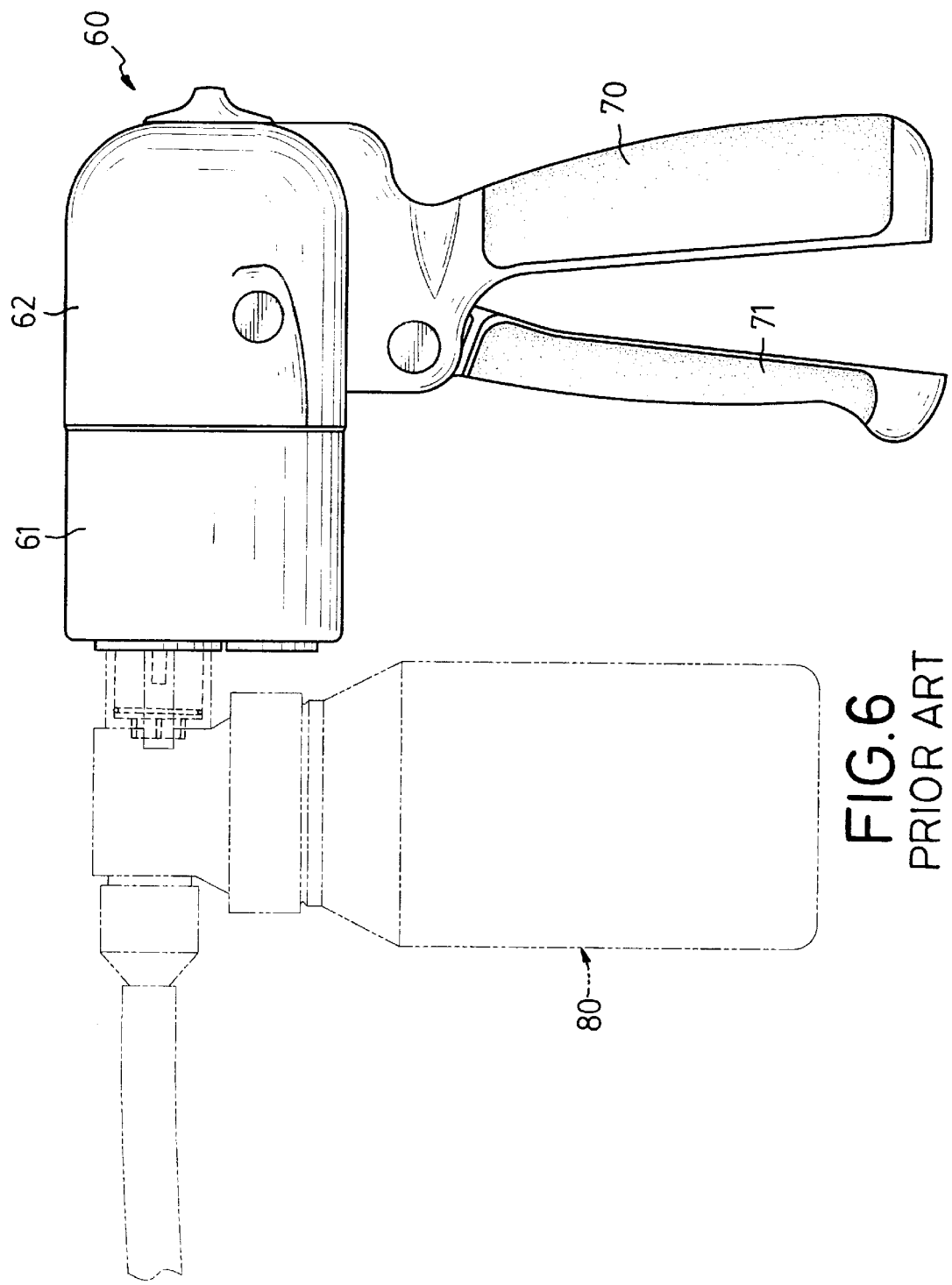
FIG. 6 is a side plan view of a conventional vacuum gun for a suction device in accordance with the prior art.
Figure 7:
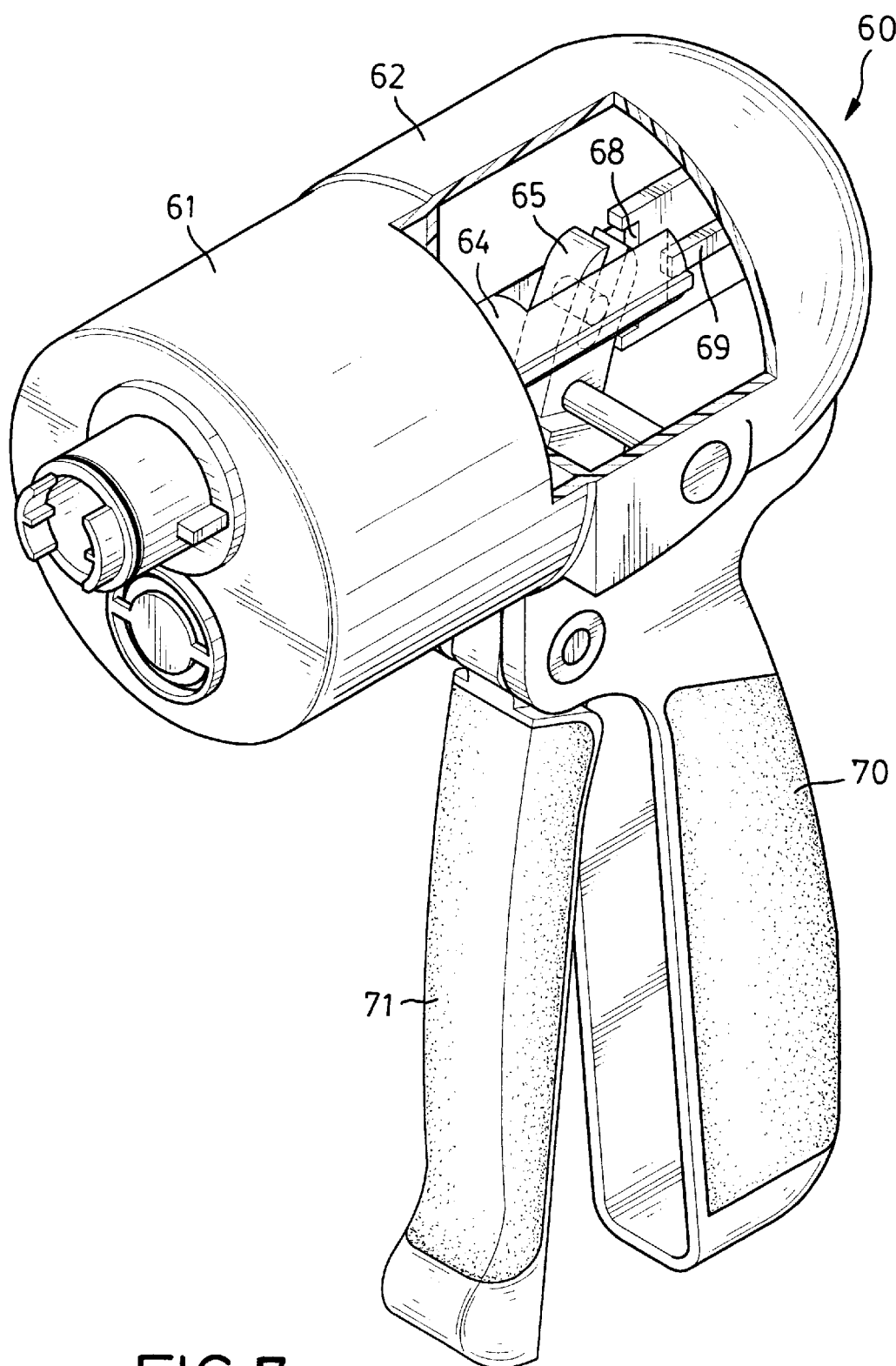
FIG. 7 is partially perspective view of a rearing housing of the conventional vacuum gun for a suction device in FIG. 6.
Figure 8:
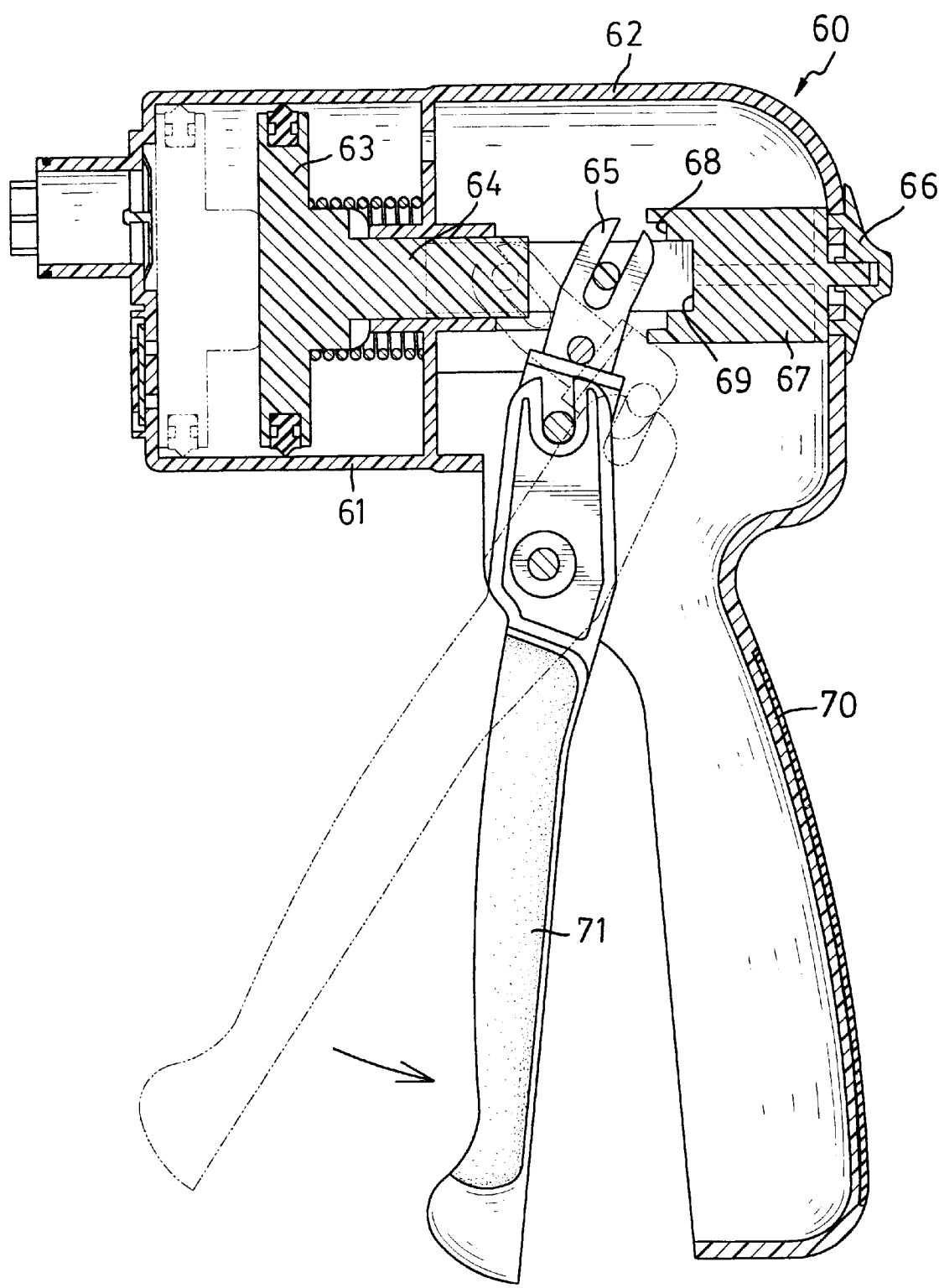
FIG. 8 is a cross-sectional side plan view of the conventional vacuum gun in FIG. 6.
Figure 9:
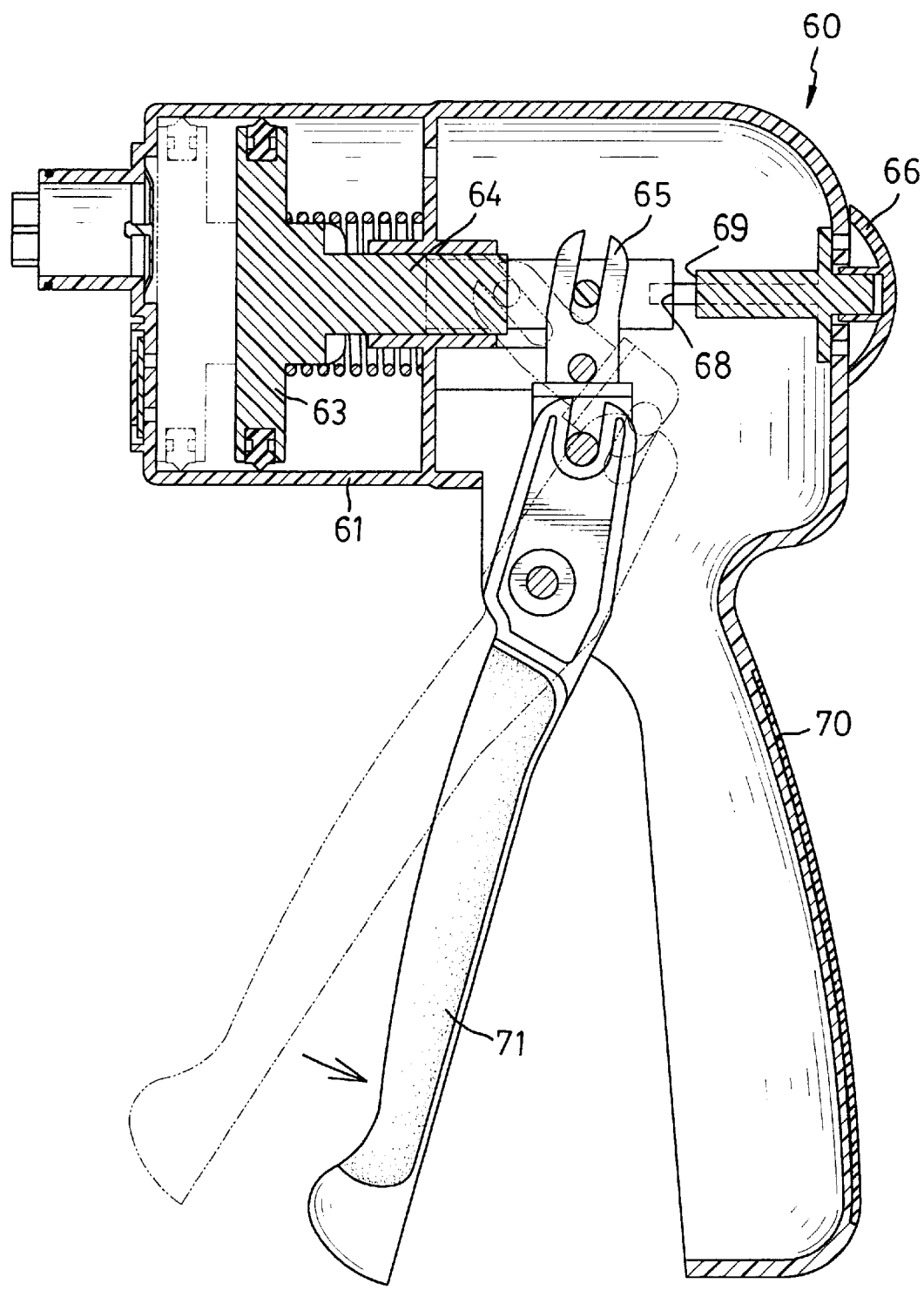
FIG. 9 is an operational cross-sectional side plan view of the conventional vacuum gun in FIG. 6.

With reference to FIG. 5, to store the vacuum gun, the slide (51) is moved out of the notch (41) in the rear housing (40) and the stub (5411) on the slide lock (541) moves into another detent (421) that holds the slide (51) away from the notch (41) in the rear housing (40). The handle (42) and the handle stop (542) are pivots away from the rear housing (40). The handle (42) pivots toward the piston housing (10) to reduce the volume of the vacuum gun and make it more convenient to store.

It should be clear to those skilled in the art that further embodiments can be made without departing from the scope and spirit of the present invention. Even though numerous characteristics and advantages of the present invention have been set forth in the foregoing description, together with details of the structure and function of the invention, the disclosure is illustrative only, and changes can be made in detail, especially in matters of shape, size, and arrangement of parts within the principles of the invention to the full extent indicated by the broad general meaning of the terms in which the appended claims are expressed.

What is claimed is:

1. An vacuum gun for a suction device comprising:
   a piston housing (10) with a front opening, a longitudinal sidewall with an inner and outer surface and a rear dividing wall with a front face and a rear face, the piston housing (10) having:
   a cap (11) covering the front opening and adapted to engage with an adapter (80);
   a knob holder (12) with a flat, central, recessed face formed on the outer surface of the longitudinal sidewall of the piston housing (10);
   multiple vacuum breaker holes (13) defined in the face in a row to communicate with the inside of the piston housing (10);

a piston (14) movably mounted inside the piston housing (10); and a drive shaft (15) having two ends with one end rigidly attached to the piston (14) and penetrating the dividing wall so the other end is inside the rear housing (40);

a suction control knob (20) rotatably mounted in the knob holder (12) to control the suction, the suction control knob (20) having:

a check valve (21) secured inside each vacuum breaker hole (13) in the knob holder (12);

multiple ventilating holes (23) defined in the suction control knob (20) to selectively communicate with the vacuum breaker holes (13); and a switch bar (22) formed on the top surface of the suction control knob (20) for user to turn the suction control knob (20) and selectively block the vacuum breaker holes (13); and a rear housing (40) attached to the piston housing (10) and having:

an inner surface and an outer surface;

a handle (42) and a trigger (43) pivotally connected to the rear housing (40); and a drive lever (151) is rotatably mounted in the rear housing (40) and having two ends with one end pivotally connected to the drive shaft (15) and the other end abuts the trigger (43).

2. The vacuum gun for a suction unit as claimed in claim 1, wherein the vacuum gun further comprises a handle lock (50) having:

a slide (51) movably attached on an outer surface of the handle (42) near a joint between the rear housing (40) and the handle (42);

a resilient stop (54) mounted inside the handle (42) and attached to the slide (51), a handle stop (542) integrally formed on the resilient stop (54) and extending toward the rear housing (40) to abut the inner surface of the rear housing (40); a slide lock (541) integrally formed on the resilient stop (54) opposite to the handle stop (542); a stub (5411) formed on a distal end of the slide lock (541);

at least one detent (421) defined in an inner surface of the handle (42) to correspond to the stub (5411) on the slide lock (541); and a notch (41) defined in the rear housing (40) near the joint to partially receive the slide (51).

3. The vacuum gun for a suction unit as claimed in claim 1, in which a resilient element (16) is mounted around the drive shaft (15) between the piston (14) and dividing wall to make the piston (14) move forward automatically.

4. The vacuum gun for a suction unit as claimed in claim 2, in which a resilient element (16) is mounted around the drive shaft (50) between the piston (14) and dividing wall to make the piston (14) move forward automatically.

5. The vacuum gun for a suction unit as claimed in claim 1, in which a frame (24) is securely attached to the outer surface of the piston housing (10) to rotatably mount the suction control knob (20) the outer side surface of the piston housing (10).

6. The vacuum gun for a suction unit as claimed in claim 2, in which a frame (24) is securely attached to the outer surface of the piston housing (10) to rotatably mount the suction control knob (20) on the outer side surface of the piston housing (10).

7. The vacuum gun for a suction unit as claimed in claim 4, in which a frame (24) is securely attached to the outer surface of the piston housing (10) to rotatably mount the suction control knob (20) on the outer side surface of the piston housing (10).

* * * * *